United States Patent [19]

Storz

[11] Patent Number: 4,656,999
[45] Date of Patent: Apr. 14, 1987

[54] CONTACT ENDOSCOPE

[76] Inventor: Karl Storz, Aufdem Schildrain 39, 7200 Tuttlingen, Fed. Rep. of Germany

[21] Appl. No.: 848,328

[22] Filed: Apr. 3, 1986

Related U.S. Application Data

[63] Continuation of Ser. No. 611,800, May 18, 1984, abandoned.

[30] Foreign Application Priority Data

Jan. 30, 1984 [DE] Fed. Rep. of Germany ..... 84100917

[51] Int. Cl.⁴ ............................................... A61B 1/00
[52] U.S. Cl. ......................................... 128/4; 128/751
[58] Field of Search ........................... 128/4-8, 128/305-318, 749-755; 30/273, 274, 282; 73/864.41

[56] References Cited

U.S. PATENT DOCUMENTS

| | | | |
|---|---|---|---|
| 2,541,246 | 2/1951 | Held | 128/305 |
| 3,173,414 | 3/1965 | Guilkert | 128/752 |
| 3,407,815 | 10/1968 | Abelson | 30/282 |
| 3,507,284 | 4/1970 | Sommers et al. | 128/318 |
| 3,896,793 | 7/1975 | Mitsui et al. | 128/6 |
| 3,924,608 | 12/1975 | Mitsui | 128/751 |
| 4,224,929 | 9/1980 | Furihata | 128/6 |
| 4,261,346 | 4/1981 | Wettermann | 128/6 |
| 4,282,884 | 8/1981 | Boebel | 128/751 |
| 4,385,810 | 5/1983 | Hamou | 350/520 |

*Primary Examiner*—Edward M. Coven
*Assistant Examiner*—Max F. Hindenburg
*Attorney, Agent, or Firm*—Donald D. Mon

[57] ABSTRACT

The invention relates to a contact endoscope for medical purposes, whose front lens or distal cover plate for the objective is brought into contact with the place to be observed.

The invention enables a sample to be taken from the observed place even during observation, or at least immediately afterwards, without having to pull the contact endoscope out of the body.

To this end a strip-blade of small wall thickness can be moved in a slideway at a small distance in front of the front lens. In this way a sample of precisely that part which has been observed is taken at a very short distance in front of the front lens.

6 Claims, 4 Drawing Figures

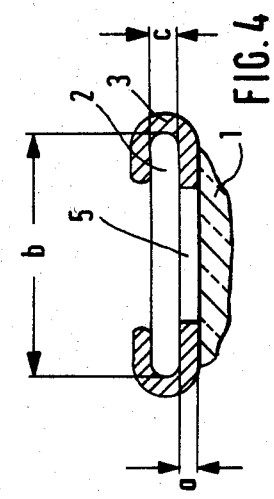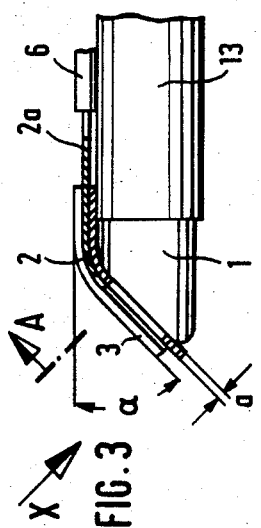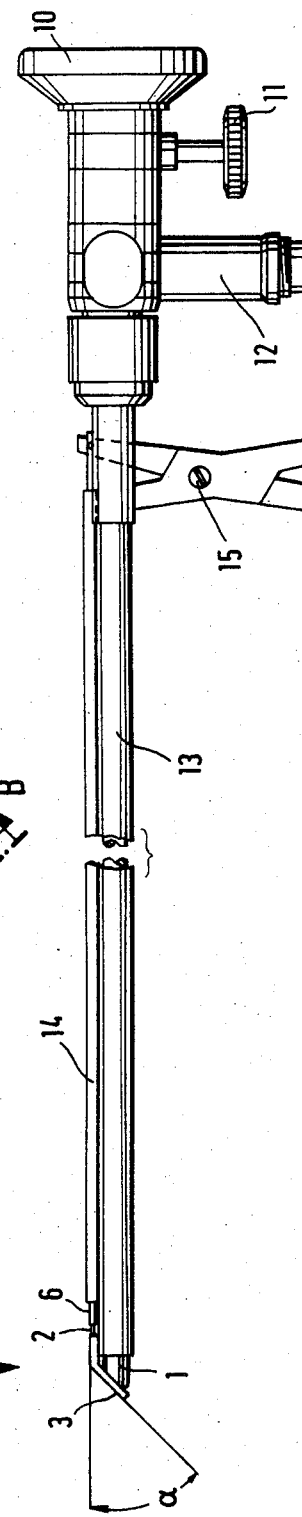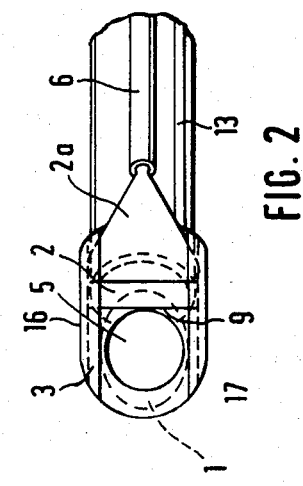

CONTACT ENDOSCOPE

This is a continuation of co-pending application Ser. No. 611,800 filed May 18, 1984, now abandoned.

FIELD OF THE INVENTION

The invention relates to a contact endoscope adapted to sever tissue which is in direct contact with the endoscope, in the path of its optical system.

BACKGROUND OF THE INVENTION

A known endoscope with panoramic view can be so altered by additions to both the objective and the eyepiece as to produce a contact endoscope of the kind specified. This gives the user the advantage that he does not need to purchase a complete contact endoscope, but can at slight expense make an existing endoscope usable for contact viewing. A large area can first be observed with low magnification, and then observation can be changed over to very high magnification on the microscopic or cellular scale over a smaller area, which is regarded as of further advantage for the examination. This enables pathological or tumour findings to be diagnosed immediately with direct observation, without requiring any ablation or operation (German OS 30 34 311.4).

With another contact endoscope the magnification can also be quickly altered. This is done by disposing a magnifying optical system with substantially higher magnification than the endoscope in a branched-off ray path which extends to an additional eyepiece. A slide is disposed transversely to the optical axis at the branching-off place, to act as an optical switch which in one operating position deflects the beam completely into the branched-off part, and in its other operative position contains a complete passage for the radiation to the other eyepiece. In this way two optical systems with different magnifications are always available and can, by very simply changing over the slide, be moved as required into the path of the beam (German OS 29 48 394.1).

Various biopsy devices for removing samples are also known. For instance, there is a tissue punch with a stripper for stripping off the tissue portions drawn in. As a result there is no need whatever to frequently pull out the punch for the removal of the punched-off tissue or bone. The pieces of tissue are accommodated in a tubular shank, where they are held fast. (German Utility Model 77 05 342).

This also ensures that the sample pieces in any case remain in the zone of the shank end, more particularly as a result of their being reliably released from the punching tool. For this purpose a spring-loaded stripper rod with a stripper is disposed at the distal end inside the punching tool. A bolt mechanism is also provided for releasing the spring-loaded stripper rod when this has reached its outermost distal position (German Utility Model 78 01 891.4).

Although it is now possible, using the already mentioned prior art contact endoscopes, to make an immediate diagnosis by direct observation of a pathological tumour tissue, there is nevertheless the need to cut a piece out of the observed zone to subject it to pathological examination.

However, this is impossible using the known biopsy tongs, since the spoon-like engaging parts of the tongs cannot be applied between the front lens of the contact endoscope and the tissue.

The invention relates to the problem of so improving the contact endoscope that a sample can be taken from the observed place even during observation, or at least immediately thereafter, without having to pull the contact endoscope out of the body.

BRIEF DESCRIPTION OF THE INVENTION

This problem is solved by providing a slideway closely spaced from the front lens or objective cover plate of the endoscope's optical system, with a strip-shaped blade therein which can be moved in a guillotine fashion to sever tissue that is in contact with the lens or cover plate, on the optical path. As a result, the surgeon can obtain a sample of precisely the observed part by the strip-shaped blade at a very short distance in front of the front lens practically even during observation.

According to a preferred but optional feature of the invention, a opening in the slideway extends around the whole distal end, so that the optical system is not occluded or reduced by the biopsy means. Moreover, in that case the sample has the shape of such opening and can be satisfactorily retained between the front lens and the blade and also readily removed from that place, the knife being moved back into its starting position after the contact endoscope has been pulled out. What takes place, therefore, is a guillotine-like parting of that portion of the tissue which is situated in the opening.

Further advantages and details of the invention can be gathered from the following description of a number of embodiments, with reference to the drawings, wherein:

BRIEF DESCRIPTION OF THE DRAWINGS

FIG. 1 is a side view of the whole contact endoscope according to the invention, FIG. 2 is a highly magnified view, taken in the direction of the arrow X in FIG. 3, FIG. 3 is a highly magnified side view exclusively of the distal end of the contact endoscope shown in FIG. 1 and FIG. 4 is a section, taken along the line A-B in FIG. 3.

DETAILED DESCRIPTION OF THE INVENTION

FIG. 1 shows a contact endoscope, the proximal end being on the right, with the eyecup 10, below which an adjusting screw 11 for fine adjustment is shown a short distance to the left. Further to the left, in the direction of the distal end 4, a connection 12 is shown for a photoconductor of known kind. So far we are dealing with a conventional contact endoscope which is known to persons skilled in the art and need not therefore be described in detail. A skilled person is also acquainted with the ray path as far as the front lens 1 with a transparent contact surface at the left-hand, distal end, so that this need not be explained. The viewing angle in relation to the longitudinal direction of the endoscope shank can be, for example, 45°, but it can be even smaller, for example, 30° or even zero, in which case the beam must be guided to the eyepiece with the eyecup 12 at right angles to the longitudinal direction of the endoscope shank 13 (sometimes called "elongated structure"), which functions as a means by which the optical system of the endoscope can be manipulated in the sense of insertion, removal, rotation, and change of angular orientation.

According to the invention the contact endoscope has a biopsy device which will now be described, as follows: The drawing shows at the left-hand, distal end 4 of the contact endoscope a slideway 3 which is disposed in front of the front lens 1 and is in contact therewith and in which a strip-shaped blade 2 of small wall thickness can be moved. At the top the slideway 3 follows the angle α and is attached to the end of the endoscope shank 13. Further to the right the strip-shaped blade 2 emerges from the slideway 3 and is attached to an actuating rod 6 lying in a guide tube 14 disposed parallel with the endoscope shank 13 for the beam.

Further to the right the actuating rod 6 is so connected to the movable half 7 of the tongs that the actuating rod 6 can be moved backwards and forwards in the longitudinal direction of the endoscope by the two halves 7,8 of the tongs. As can be seen, the movable half 7 of the tongs can be pivoted around the pivot 15.

A skilled addressee is basically acquainted with actuating tongs of this kind, which need therefore not be described in detail. Some other actuating device might also be provided for moving the actuating tongs 6. FIG. 1 shows the opened position of the tongs, in which the strip-shaped blade 2 is in its withdrawn, inoperative position. When the movable half 7 of the tongs is forced to the right on to the half 8, the rod 6 is pushed to the left, as a skilled person will readily understand.

FIG. 2 is a highly magnified view taken in the direction of arrow X in FIG. 3 of the distal end shown in FIG. 3. As a result FIG. 2 is a plan view of the slideway 3. Its centre is formed with an opening 5 through which the front lens 1 is visible. Further to the right is cutting edge 9 of the strip-shaped blade 2, whose width b (FIG. 4) decreases in the direction of the rod 6. As a result of this step, the distal end of the endoscope is better adapted to the external dimensions, since the rod 6 has a very much smaller diameter than the endoscope shank 13 for the beam. This transitional zone of the blade 2 is denoted by the reference 2a. In this position of the blade 2, the transitional zone lies substantially outside the slideway 3.

In this view the external contours of the slideway 3 are preferably oblong—i.e., the side edges 16 and 17 are parallel straight lines interconnected by a radius which corresponds to half the distance of the two straight lines from one another.

FIG. 3 shows how the slideway 3 extends in an arc around the angle α and is attached to the endoscope shank 13 and also to the front lens 1. In the zone of the blade 2, the slideway 3 is shown sectioned, to indicate how the blade lies when thus withdrawn, since the blade 2 is resilient, and in this inoperative position is already bent by the angle α in the slideway 3. The blade 2 is at a very short distance a from the front lens 1. The distance corresponds substantially to the wall thickness of the slideway 3, as can be gathered from FIG. 4. The distance is a small fraction of a millimeter. If, for example, the blade 2 has a thickness of 0.10 mm, which is already relatively thick, the distance a is also only about 0.1 mm thick. In that case the whole slideway 3 has a thickness of 0.3 mm. However, for example, razor blades of course have an even much smaller wall thickness and are also resilient. In the present case, however, we are dealing with a strip-shaped blade 2 whose resilience or flexibility is even greater than that of a razor blade.

FIG. 4 is a section, taken along the line A-B in FIG. 3. The section therefore passes through the centre of the opening 5, so that the blade 2 is shown in its full width b. The blade has a wall thickness c which is of substantially the same order of magnitude as the wall thickness a of the slideway 3 which extends around the outside edges of the blade. It can also be clearly seen that the slideway 3 bears against the front lens 1, and can also be attached thereto. On the other hand, in another embodiment a spaced-out distance can be produced between the slideway 3 and the front lens 2, for which purpose spacing members might be disposed between the slideway 3 and the front lens 1.

The wall thickness of the sample cut off is determined in accordance with the distance a between the blade 2 and the front lens 1. Because, since this is a contact endoscope, the part to be observed passes through the opening 5 and comes into contact with the front lens 1 or the cover plate (cf. also FIG. 2). If then a sample is to be removed, the halves 7,8 of the tongs are compressed, so that the blade is forced forwards by the actuating rod 6. As a result, the cutting edge 9 (FIG. 2) acts like a guillotine to cut a circular disc off the observed piece. This disc corresponds to the opening 5 and the distance a between the blade 2 and the front lens 1. Then the endoscope is pulled out. As a result of the return of the tongs into the starting position (FIG. 1), the blade releases the sample lying in the opening, so that the sample can then easily be removed.

The overall arrangement can also be accommodated in an oval outside shank, more particularly since the aforementioned endoscope shank 13 contains only the ray path, and not the other members.

The invention is not limited to the embodiments illustrated or described, but the skilled person can produce variants thereof within the scope of the claims.

I claim:

1. An endoscope for contact endoscopy, said endoscope having a proximal end and a distal end, and comprising an optical system with an optical axis, said optical system terminating with an exposed transparent surface located at or adjacent to said distal end, said transparent surface intended to be pressed directly into surface-to-surface contact with an area of tissue to be observed and to be severed at that area for biopsy purposes while still in surface-to-surface contact with said transparent surface, elongated structure having an axis of elongation and mounting said optical system by which the optical system can be physically manipulated, said axes being parallel; and means for severing a layer of tissue including said area while in contact with said surface comprising a slideway spaced from and straddling said transparent surface, and having an aperture therethrough which enables said area of said tissue to pass through said slideway to make said surface-to-surface contact with said transparent surface thereby to be observed, a strip-shaped cutter blade slidably mounted in said slideway adapted to be moved across said aperture whereby to sever a layer of said tissue including said area while in contact with said transparent surface and still in view therethrough while being cut off, and actuating means so as to move said blade in said slideway.

2. A contact endoscope according to claim 1 in which said aperture is substantially circular, its boundary extending around said optical axis.

3. A contact endoscope according to claim 1 in which said axis of elongation and said slideway from an acute angle with one another, and in which said blade is sufficiently flexible that it can bend to said angle.

4. A contact endoscope according to claim 1 in which said actuating means is a rod movable parallel to said axis of elongation, connected to said blade.

5. A contact endoscope according to claim 3 in which said actuating means is a rod movable parallel to said axis of elongation, connected to said blade.

6. A contact endoscope according to claim 4 in which actuating tongs are connected to said rod to move said rod.

* * * * *